United States Patent
Yasuhara et al.

(10) Patent No.: US 9,612,227 B2
(45) Date of Patent: Apr. 4, 2017

(54) ULTRASONIC PROBE

(71) Applicant: HITACHI ALOKA MEDICAL, LTD., Tokyo (JP)

(72) Inventors: Takeo Yasuhara, Tokyo (JP); Hidetsugu Katsura, Tokyo (JP); Toru Watanabe, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 204 days.

(21) Appl. No.: 14/438,795

(22) PCT Filed: Oct. 30, 2013

(86) PCT No.: PCT/JP2013/079350
§ 371 (c)(1),
(2) Date: Apr. 27, 2015

(87) PCT Pub. No.: WO2014/069501
PCT Pub. Date: May 8, 2014

(65) Prior Publication Data
US 2015/0276685 A1 Oct. 1, 2015

(30) Foreign Application Priority Data

Oct. 31, 2012 (JP) .................................. 2012-240497
Mar. 5, 2013 (JP) .................................. 2013-043106

(51) Int. Cl.
*G01N 29/24* (2006.01)
*A61B 8/12* (2006.01)
(Continued)

(52) U.S. Cl.
CPC .............. *G01N 29/24* (2013.01); *A61B 8/12* (2013.01); *A61B 8/445* (2013.01); *A61B 8/4483* (2013.01);
(Continued)

(58) Field of Classification Search
USPC ......................................................... 73/632
See application file for complete search history.

(56) References Cited

U.S. PATENT DOCUMENTS

| 2003/0028108 | A1 | 2/2003 | Miller |
| 2012/0150038 | A1 | 6/2012 | Osawa |
| 2014/0375171 | A1* | 12/2014 | Tai ...................... H01L 41/0825 |
| | | | 310/341 |

FOREIGN PATENT DOCUMENTS

| CN | 102525557 A | 7/2012 |
| JP | 61-268238 A | 11/1986 |

(Continued)

OTHER PUBLICATIONS

Notification of Transmittal of Translation of the International Preliminary Report on Patentabililty (Form PCT/IB/338) of International Application No. PCT/JP2013/079350 mailed May 14, 2015 with Forms PCT/IB/373, PCT/IB/326 and PCT/ISA/237, with translation. (9 pages).

(Continued)

*Primary Examiner* — John Chapman, Jr.
(74) *Attorney, Agent, or Firm* — Westerman, Hattori, Daniels & Adrian, LLP

(57) ABSTRACT

A probe that is inserted into a body cavity, wherein an inner unit (inner assembly) comprises an oscillator unit, an intermediate substrate, an electronic circuit substrate, and a backing member. An exhaust heat sheet is joined to an area at the perimeter of the rear surface of the electronic circuit substrate. The exhaust heat sheet comprises a main body part and a plurality of wings that extend to the outside from the main body part. The plurality of wings include a right wing and a left wing. The wings are inserted into two slits formed in a probe head case (heat radiating shell), and the end parts of the wings are accommodated in and adhered to two recessed sections formed in the outer surface of the probe (Continued)

head case. Thus, heat generated inside the probe head case can be directly transferred to the outer surface of the probe head case.

7 Claims, 15 Drawing Sheets

(51) Int. Cl.
    *A61B 18/04*     (2006.01)
    *A61N 7/00*     (2006.01)
    *G01N 29/32*     (2006.01)
    *A61B 8/00*     (2006.01)

(52) U.S. Cl.
    CPC ............... *A61B 18/04* (2013.01); *A61N 7/00* (2013.01); *G01N 29/32* (2013.01); *A61B 8/4494* (2013.01); *A61B 8/546* (2013.01)

(56) References Cited

FOREIGN PATENT DOCUMENTS

| JP | 10-075953 A | 3/1998 |
|---|---|---|
| JP | 2001-074710 A | 3/2001 |
| JP | 3420954 B2 | 6/2003 |
| JP | 2005-507581 A | 3/2005 |
| JP | 2006-129965 A | 5/2006 |
| JP | 2007-158468 A | 6/2007 |
| JP | 2008-86653 A | 4/2008 |
| WO | 03/013181 A2 | 2/2003 |

OTHER PUBLICATIONS

Office Action dated Apr. 29, 2016, issued in counterpart Chinese Patent Application No. 201380057151.4, with English translation. (11 pages).
International Search Report dated Jan. 14, 2014, issued in corresponding application No. PCT/JP2013/079350.

* cited by examiner

ULTRASONIC PROBE

TECHNICAL FIELD

The present invention relates to an ultrasonic probe, and in particular, to a body cavity insertion type ultrasonic probe having a two-dimensional array transducer.

BACKGROUND ART

In the medical field, ultrasound diagnostic apparatuses are being used. An ultrasound diagnostic apparatus is a device that transmits and receives ultrasound to and from a living body, and forms an ultrasound image based on a reception signal obtained by the transmission and reception of the ultrasound. The transmission and reception of the ultrasound are executed by an ultrasonic probe. Various probes are commercialized, including a body cavity insertion type probe. The body cavity insertion type probe is inserted into the esophagus, the rectum, the vagina, or the like, and transmits and receives the ultrasound inside the body. Of these, the esophagus probe is a probe inserted into the esophagus, and more specifically, is a probe that transmits and receives ultrasound to and from the heart, while in the esophagus.

In recent years, three-dimensional ultrasound diagnosis is becoming more wide-spread. In this technique, ultrasound is transmitted and received to and from a three-dimensional space in a living body, to acquire volume data, and the volume data are used to form a three-dimensional image representing the three-dimensional space, a two-dimensional tomographic image representing an arbitrary cross section of the three-dimensional space, or the like. In order to transmit and receive the ultrasound to and from the three-dimensional space, in a probe head, in general, a two-dimensional array transducer is provided. The two-dimensional array transducer is formed by a plurality of transducer elements (for example, a few thousand transducer elements) arranged two-dimensionally.

Patent Document 1 discloses an esophagus probe for three-dimensional ultrasound diagnosis. A transducer unit is placed in the head of the esophagus probe. The transducer unit comprises a two-dimensional array transducer, an interface layer, an electronic circuit (integrated circuit), a backing layer, a heat sink, or the like, provided in that order from the side of a living tissue. The electronic circuit is a circuit that executes channel reduction; that is, a circuit for reducing the number of signal lines. The heat sink is a circuit that takes away heat generated in the electronic circuit.

RELATED ART REFERENCE

Patent Document

[Patent Document 1] JP 2005-507581 A

DISCLOSURE OF INVENTION

Technical Problem

When an electronic circuit board is to be provided in the probe head, because a significant amount of heat is generated in the electronic circuit board, heat dissipation from the electronic circuit board becomes a problem. Specifically, when the heat generated in the electronic circuit board is conducted to the two-dimensional array transducer, the temperature of the two-dimensional array transducer becomes high, resulting in a problem such as degradation of the two-dimensional array transducer and an increase in the temperature of the transmission/reception surface. In consideration of this, in order to avoid, as much as possible, the conduction of the heat generated in the electronic circuit board to the two-dimensional array transducer, it becomes necessary to discharge the heat from the electronic circuit to other members.

However, in the esophagus probe described in Patent Document 1, because the heat sink is provided on the back surface side of the electronic circuit board with a backing layer therebetween, there is a problem in that it is difficult to increase the heat conduction efficiency from the electronic circuit board to the heat sink.

Solution to Problem

An advantage of the present invention is that heat generated in an inner unit is effectively discharged to other members.

According to one aspect of the present invention, there is provided an ultrasonic probe comprising: an inner unit including an array transducer having a plurality of transducer elements, an electronic circuit board provided on a side of a back surface of the array transducer and having an electronic circuit which is electrically connected to the plurality of transducer elements, and a heat dissipation sheet that conducts heat from the electronic circuit board; and a probe head case that houses the inner unit, wherein the heat dissipation sheet comprises: a body portion that receives the heat from the electronic circuit board; and a wing which is a portion to which heat from the body portion is conducted and which extends from the body portion toward an outer side, the probe head case has an opening structure, and the wing is inserted into the opening structure and is joined to the probe head case.

According to the above-described configuration, the heat generated in the electronic circuit board in an inner unit (for example, an inner assembly, an inner layered structure) can be conducted through the heat dissipation sheet to the probe head case. The heat dissipation sheet comprises a body portion and at least one wing, and the heat received at the body portion is conducted to the wing, and further from the wing to the probe head case joined to the wing. In the probe head case, an opening structure is formed, which has an opening which is at least in communication with the inner side of the probe head case. The wing is inserted into the opening. An end of the wing preferably extends to the outer side of the probe head case, and is joined to the outer surface of the probe head case, or inserted; that is, embedded, into a gap formed inside the probe head case. In general, in the probe head case housing a heat generating structure, the outer surface has a lower temperature than the inner surface, and, with the use of the heat dissipation sheet, the heat can be conducted directly to the outer surface or to the inside without passing through the inner surface of the probe head case. In other words, for the heat dissipation, the temperature inclination can be actively used. Alternatively, a configuration may be employed in which, in addition to the above-described heat conduction, the heat from the inner unit is conducted to the inner surface of the probe head case. Alternatively, a configuration may be employed in which a part of the plurality of the wings are joined to the inner surface of the probe head. In either case, with the active heat conduction to the portion having a lower temperature, the heat can be effectively dissipated from the electronic circuit board.

Preferably, the heat dissipation sheet is directly or indirectly joined to the back surface of the electronic circuit board. In this case, in order to secure propagation of the ultrasound from the electronic circuit board to the backing member, an opening is preferably formed on the heat dissipation sheet, through which a part of the backing member passes. Alternatively, the heat dissipation sheet maybe placed on the front surface side (transmission/reception side) of the electronic circuit board. In any case, as the heat dissipation sheet, preferably, a structure with superior thermal conductivity is used.

According to another aspect of the present invention, preferably, at least the wing in the heat dissipation sheet is flexible. According to such a configuration, superior assembly operability can be achieved, and it becomes easy to realize close contact between the wing and the probe head case . For the fixation of the wing, preferably, an adhesive having superior thermal conductivity is used. Alternatively, other fixation methods such as fitting, screwing, welding, or the like may be employed.

According to another aspect of the present invention, preferably, the heat dissipation sheet has a right side wing and a left side wing that extend from the body portion toward a right side and a left side, respectively, the probe head case has a right side opening structure and a left side opening structure, the right side wing is inserted into and fixed on the right side opening structure, and the left side wing is inserted into and fixed on the left side opening structure. According to such a configuration, the heat can be conducted using a plurality of wings, resulting in improved heat dissipation efficiency. In particular, because the heat can be dissipated on both sides of the inner unit, the temperature increase of the electronic circuit board as a whole can be effectively inhibited. Normally, a width in a left-and-right direction inside the probe head case is not too wide, and thus, if heat is dissipated from the right side and the left side of the electronic circuit board, the heat conduction distance from the electronic circuit board to the probe head case (outer surface or inside) can be reduced.

According to another aspect of the present invention, preferably, the right side opening structure and the left side opening structure are respectively a right side slit and a left side slit in communication with an inside and an outside of the probe head case, the right side wing is inserted into the right side slit and is fixed on an outer surface of the probe head case, and the left side wing is inserted into the left side slit and is fixed on the outer surface of the probe head case. According to such a configuration, the heat from the electronic circuit board is conducted to the outer surface of the probe head through the right side wing and the left side wing; that is, through the right side slit and the left side slit. In the probe head case, the temperature of the outer surface is in general lower than the temperature of the inner surface facing the heat generating structure, and thus, the heat can be directly discharged to such a portion having a lower temperature and the heat dissipation efficiency can be improved.

According to another aspect of the present invention, preferably, a right side recess in communication with the right side slit is formed on the outer surface of the probe head case, and an end of the right side wing is housed in the right side recess, and a left side recess in communication with the left side slit is formed on the outer surface of the probe head case, and an end of the left side wing is housed in the left side recess. According to such a configuration, a problem in that bulging of the ends is caused on the outer surface of the probe head and smoothness of the outer shape of the probe head is disturbed can be solved or mitigated. In particular, in the body cavity insertion type ultrasonic probe, it is strongly desired to smoothen the shape of the probe head, and, with the above-described configuration, such a desire can be satisfied.

According to another aspect of the present invention, preferably, the wing comprises: a first portion having a lateral width which allows the wing to pass through the opening structure; and a second portion which is a portion connected to the first portion, which can be opened, which has a greater lateral width than that of the first portion in an open state, and which is fixed on the outer surface of the probe head case in the open state. According to such a configuration, because the second portion is formed as a portion which can be opened, the second portion can be opened after the second portion which is in a folded state is inserted into the opening structure, and the second portion can be fixed on the outer surface of the probe head. In other words, a size (contact area) of a portion of the wing contacting the outer surface of the probe head case can be increased, regardless of the size of the opening structure.

According to another aspect of the present invention, preferably, the probe head case is formed from a first case portion and a second case portion, a gap is formed in the opening structure between the first case portion and the second case portion, and the wing is inserted into the gap. According to such a configuration, both surfaces of the wing can be used as the heat conduction surfaces. In addition, the wing can be sandwiched and fixed when the first case portion and the second case portion are combined.

The electronic circuit described above forms at least one of a transmission signal processing circuit and a reception signal processing circuit, and preferably forms both processing circuits. The electronic circuit is preferably a channel reduction circuit. The channel reduction circuit generates, during transmission, a plurality of transmission drive signals from one transmission trigger signal for the array transducer as a whole or in a predetermined unit, and generates, during reception, one group reception signal from a plurality of reception signals in a predetermined unit. Preferably, the electronic circuit board is a semiconductor board on a surface of which an electronic circuit is formed and that does not have a thick package. Such an electronic circuit board may be directly joined on the back surface side of the array transducer, but preferably, the electronic circuit board is connected to the array transducer with an interface board therebetween. As the interface board, there may be used a board which has a wiring converting function or the like. When the thermal conductivity of the heat dissipation member such as the heat dissipation sheet is higher than the thermal conductivity of the interface board, the heat generated in the electronic board can be more readily moved to the heat dissipation member. The array transducer is in general formed from a material having a piezoelectric characteristic, and a MUT (Micro-Machined Ultrasonic Transducer) may be used. Preferably, the probe head case is a skeleton of the probe head and, at the same time, a heat discharge member. The probe head case is formed with a member having a large surface area and superior thermal conductivity. With the use of such a heat discharge structure, it becomes possible to inhibit the temperature increase of the electronic circuit board while discharging the heat from the entirety of the heat discharge structure to the environment and without causing a local temperature increase. The ultrasonic probe is preferably a body cavity insertion type probe, and more preferably a transesophageal probe having a 2D array transducer.

EMBODIMENT

A preferred embodiment of the present invention will now be described with reference to the drawings.

Figure 1:
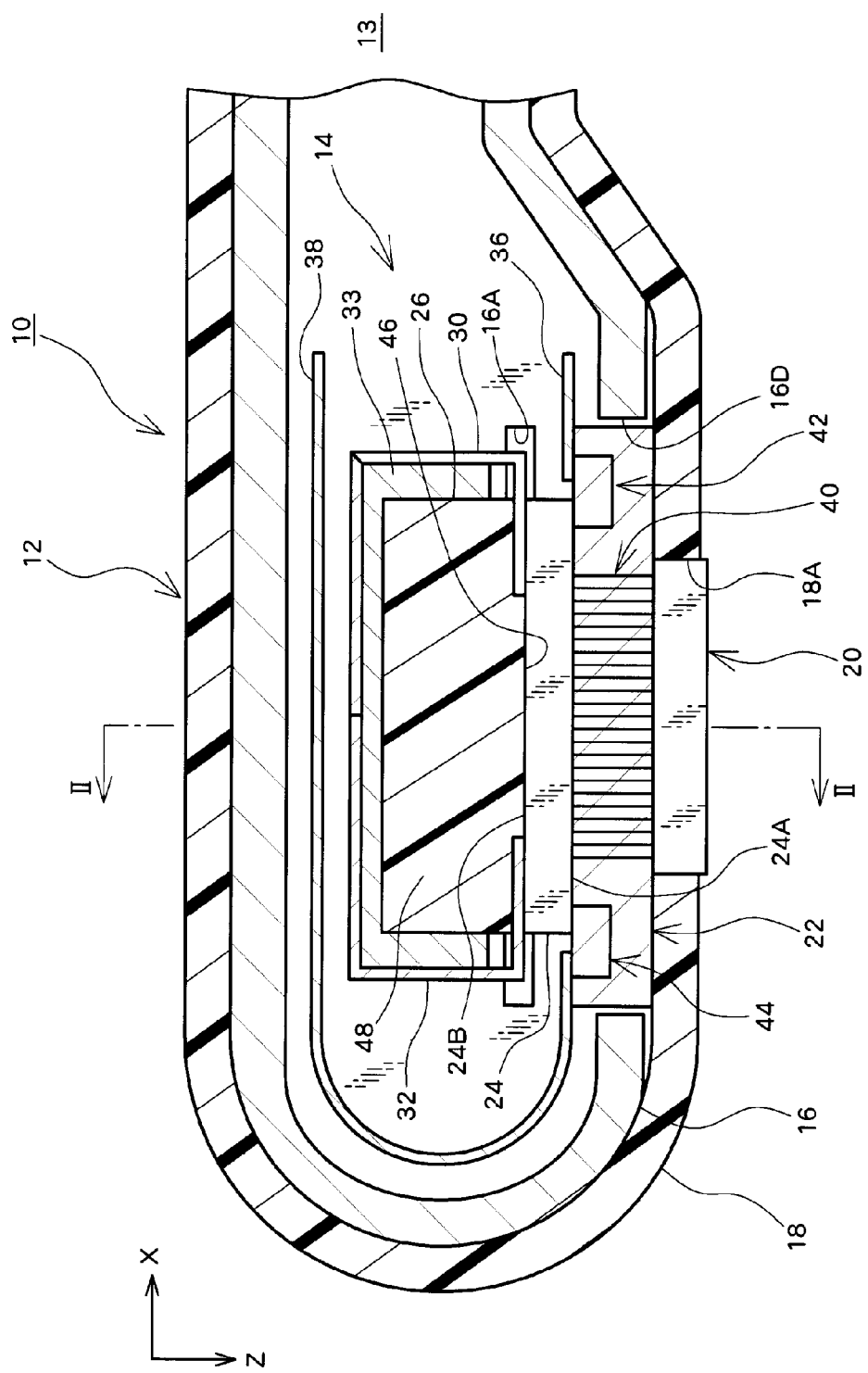
FIG. 1 is an XZ cross sectional diagram showing a preferred embodiment of a body cavity insertion type probe according to the present invention.

FIG. 1 shows an ultrasonic probe of a preferred embodiment according to the present invention. FIG. 1 is a cross sectional diagram (XZ cross sectional diagram) of the ultrasonic probe. The ultrasonic probe is a body cavity insertion type probe, and, in particular, an esophagus probe.

In FIG. 1, a probe 10 comprises a probe head 12, an insertion tube 13, an operation unit, a probe cable, etc. In the present embodiment, the probe head 12 is a portion that is inserted into the esophagus in the living body and that transmits and receives ultrasound while in the esophagus. During the ultrasound diagnosis, the probe head 12 is positioned in the esophagus such that a site to be diagnosed in a heart is included in a three-dimensional space which is an ultrasound transmission/reception region.

The inside of the probe head 12 is hollow, and an inner assembly 14 is placed therein. Alternatively, a filler material such as a resin may be filled around the inner assembly 14. The inner assembly 14 transmits and receives ultrasound in a Z direction; that is, a downward direction in FIG. 1. An X direction is a central axis direction of the probe head 12, the Z direction is the transmission/reception direction, and a Y direction is defined as a direction orthogonal to the X direction and the Z direction. The inner assembly 14 is more specifically placed inside a heat discharge shell 16. The heat discharge shell 16 is a hard, hollow container formed by a heat conductive member such as copper, and forms a probe head case. In other words, the heat discharge shell 16 forms an outer skeleton or a structure in the probe head 12. On an outer side of the heat discharge shell 16, an outer skin 18 is provided which is relatively soft and which is formed from a resin or the like having an insulating characteristic. On a side of the living body tissue of the heat discharge shell 16, an opening 16D is formed, and a part of the inner assembly 14 protrudes to the outer side of the heat discharge shell 16 through the opening 16D. The inner assembly 14 comprises a transducer unit 20, an interface board 22, an electronic circuit board 24, a backing member 26, a heat dissipation sheet having a plurality of wings, a backing case 33, etc., as will be described below. These members will be described below in detail.

As will be described later with reference to FIG. 4, the array transducer is formed by a plurality of transducer elements arranged along the X direction and the Y direction, and more specifically, is formed by a few thousand transducer elements. An ultrasound beam is formed by the array transducer and is electrically scanned. As the method of electrical scanning, an electron sector scanning method or the like is known. In the present embodiment, the ultrasound beam can be two-dimensionally scanned, and, with such a scan, a three-dimensional space is formed. A three-dimensional ultrasound image or the like representing the three-dimensional space can be formed by processing volume data acquired from the three-dimensional space. As shown in FIG. 1, on the side of the living body of the outer skin 18, an opening 18A is formed, and a part of the transducer unit 20 on the living body side expands and extends from the opening 18A to the living body side. In the execution of the ultrasound diagnosis, a state is created in which a surface of the transducer unit 20 on the living body side; that is, the transmission/reception surface, is in close contact with the inner surface of the esophagus which is a living body tissue surface.

On the back surface side of the transducer unit 20; that is, the upper side in FIG. 1, the interface board 22 is provided. The interface board 22 has a function to electrically connect the array transducer and an electronic circuit formed on the electronic circuit board 24. In the present embodiment, the interface board 22 is formed by a multilayer board, and has a lead array 40. The lead array 40 consists of a plurality of signal lines that electrically connect between the plurality of transducer elements and a plurality of terminals on the electronic circuit. The interface board 22 may alternatively be an interposer having an arrangement conversion function. That is, the electrode arrangement on the side of the array transducer and the electrode arrangement on the side of the electronic circuit may differ from each other. In the present embodiment, the interface board 22 also has a function to connect flexible boards 36 and 38 to be described below and the electronic circuit, and, for this purpose, groups of connection lines 42 and 44 are provided in the interface board 22. As shown in FIG. 1, the interface board 22 is placed in the opening 16D formed in the heat discharge shell 16. The basic material of the interface board 22 is, for example, ceramic having an insulating characteristic.

On the back surface side of the interface board 22; that is, the upper side in FIG. 1, the electronic circuit board 24 is provided. The electronic circuit board 24 has an electronic circuit for channel reduction. Specifically, the electronic circuit generates, during transmission, a plurality of transmission drive signals based on a transmission trigger signal transmitted from a side of a device body for the array transducer as a whole or in a predetermined unit, and supplies the transmission drive signals to the array transducer. During reception, the electronic circuit executes a phased summing process for a plurality of reception signals in units of element group, and generates a group reception signal. By providing such a channel reduction circuit, it is possible to significantly reduce the number of signal lines connected to the probe head. For example, the signals for all transducer elements, which are provided in a few thousand in number, can be processed by connecting only about 100 signal lines. In the present embodiment, the electronic circuit board 24 is formed by a substantially exposed semiconductor board on a surface of which the electronic circuit is formed. In other words, a package functioning as an outer cover is not provided, and the entirety of the semiconductor board is protected by a thin protection layer. On a surface 24A of the electronic circuit board 24 on the living body side, a plurality of electrodes corresponding to the plurality of transducer elements are formed. The lead array 40 described above is connected to the plurality of electrodes. A thickness of the electronic circuit board 24 in the Z direction is, for example, about 0.6 mm. A thickness of the above-described interface board 22 in the Z direction is, for example, about 1 mm.

On a back surface 24B of the electronic circuit board 24, there are set an ultrasound propagation region which is a center region and a heat dissipation region which is a peripheral region. The backing member 26 is joined to the ultrasound propagation region. More specifically, the backing member 26 is formed by a block-shaped body 48 and a protrusion 46 formed on the living body side of the body 48, and a surface of the protrusion 46 on the living body side is joined to the ultrasound propagation region. The heat dissipation sheet is joined to the peripheral region, as will be described later in detail. More specifically, the heat dissipation sheet has an opening, the protrusion 46 is joined to the center part on the back surface side of the electronic circuit board 24 through the opening, and, with such a configuration, the heat dissipation sheet is sandwiched between the body 48 of the backing member 26 and the heat dissipation region which is the peripheral region of the electronic circuit board 24. The heat dissipation sheet has a rear wing 30 and a front wing 32 shown in FIG. 1. In addition, the heat dissipation sheet also has a right wing and a left wing, which are not shown in FIG. 1. The backing member 26 scatters and attenuates unnecessary ultrasound emitted to the back surface side. For example, the backing member 26 has an acoustic attenuation characteristic of about 6~15 dB/cmMHz.

The backing member is formed, for example, by mixing tungsten, a tungsten compound, or the like into a resin. In this case, as the resin, there may be exemplified a thermoplastic resin such as nylon, polyethylene, polypropylene, polystyrene, or the like; a thermosetting resin such as an epoxy resin, a phenol resin, a urea resin, a melanin resin, or the like; and various rubbers. In manufacturing the backing member, in order to realize a desired acoustic impedance and a desired acoustic attenuation characteristic, a suitable amount of powder of tungsten, the tungsten compound, or the like is mixed into the resin. Alternatively, other materials may be mixed.

The heat dissipation sheet described above is formed, for example, from a carbon sheet, a graphite sheet, a sheet made of a metal such as copper, or the like, and is formed from a material having superior thermal conductivity. A thickness of the backing member 26 in the Z direction is, for example, about 3 mm.

Figure 2:
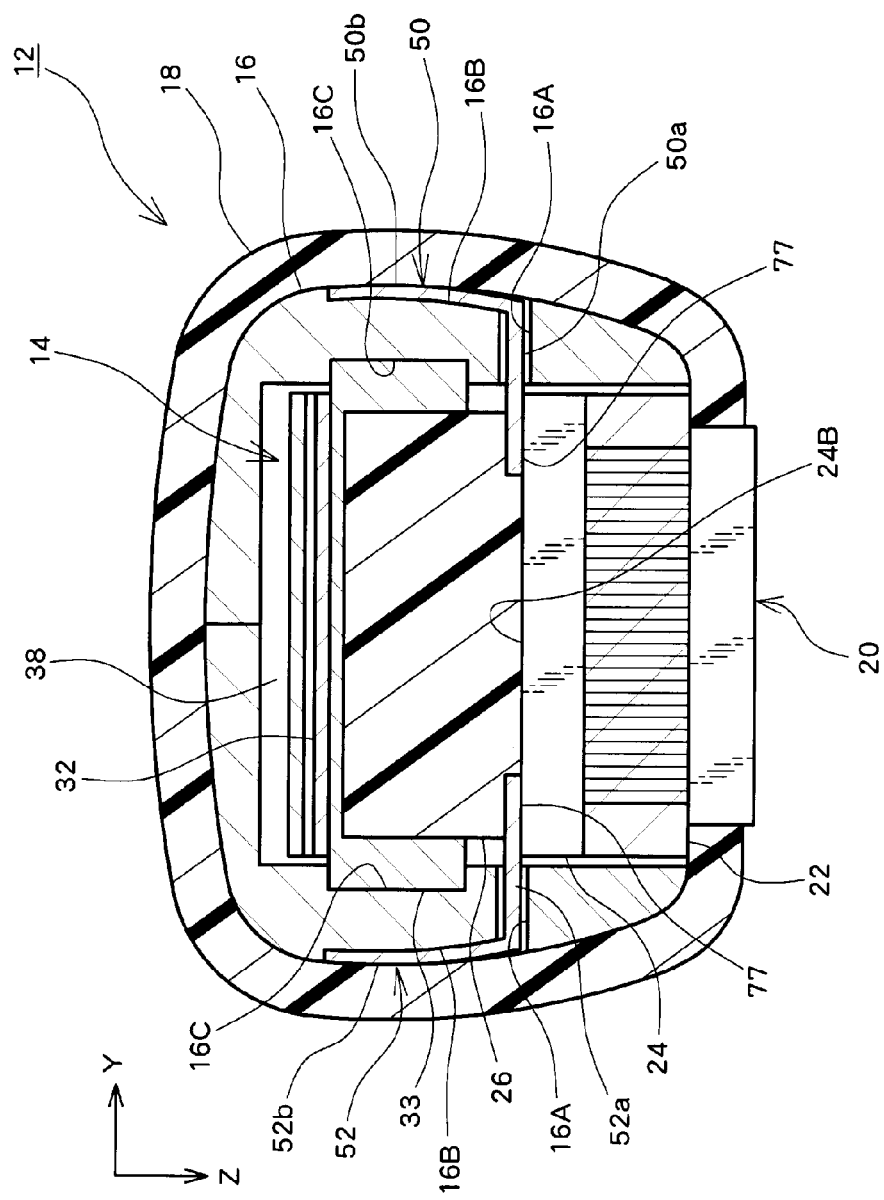
FIG. 2 is a YZ cross sectional diagram of the probe shown in FIG. 1.

The backing member 26 is surrounded by the backing case 33 except for the end on the living body side. That is, the body 48 of the backing member 26 is housed in the backing case 33. The backing case 33 functions as a heat conductive member and a jig. In the present embodiment, the rear wing 30 and the front wing 32 in the heat dissipation sheet are folded in a manner to extend along the outer surface of the backing case 33, and are adhered on the outer surface of the backing case 33. Therefore, the heat moves from the back surface side of the electronic circuit board 24 to the backing case 33 through the rear wing 30 and the front wing 32. As shown in FIG. 2 described below, the backing case 33 is joined and fixed to the heat discharge shell 16, and heat conduction occurs from the backing case 33 to the heat discharge shell 16. In addition, the heat discharge shell 16 holds and fixes the backing case 33 in the probe head 12. In addition to the above, heat is conducted from the back surface side of the electronic circuit board 24 to the heat discharge shell 16 through the right wing and the left wing of the heat dissipation sheet, as will be described below in detail.

On the ends on the back surface side of the interface board 22; that is, a non-living body side, flexible boards 36 and 38 are connected. Each of the flexible boards 36 and 38 is formed from an FPC (flexible printed circuit board), and has a wiring pattern. A plurality of signal lines are connected to the ends of the flexible boards 36 and 38 on the side of the device body. However, these signal lines are not shown in FIG. 1. Alternatively, the plurality of signal lines may be connected to the flexible boards 36 and 38 by means of a connector. As shown in FIG. 2, in the heat discharge shell 16, a slit 16A is formed on each of the side surfaces on both sides in the Y direction. The right wing and the left wing to be described later are inserted into the two slits 16A. In the present embodiment, the flexible board 38 is provided in addition to the flexible board 36, in order to reliably connect a large number of signal lines. As shown in FIG. 1, the flexible board 38 extends from a tip edge on the interface board 22 to the upper part, passes on the back surface side of the inner assembly 14; that is, the upper part in FIG. 1, and extends toward the body of the ultrasound diagnostic apparatus. Alternatively, the flexible board 38 may be omitted so long as the connection of the plurality of signal lines can be reliably achieved.

FIG. 2 shows a cross section in a direction shown by II in FIG. 1; that is, the YZ cross section. As already described, the probe head 12 has the heat discharge shell 16. The heat discharge shell 16 functions as a heat conductive structure; that is, a heat discharge structure, and also as a probe head case. The heat discharge shell 16 is covered by the outer skin 18. The inner assembly 14 is provided inside the probe head 12, and comprises the transducer unit 20, the interface board 22, the electronic circuit board 24, the backing member 26, and the backing case 33, provided in that order from the living body side. The heat dissipation sheet is sandwiched between the electronic circuit board 24 and the backing member 26. The heat dissipation sheet includes a body portion 77 serving as a heat reception portion, and a plurality of wings connected thereto. The plurality of wings more specifically include the rear wing and the front wing described above, and the right wing 50 and the left wing 52 shown in FIG. 2. The right wing 50 and the left wing 52 are inserted into a pair of the slits 16A formed on right and left side walls of the heat discharge shell 16. Each slit 16A is a through channel extending along the X direction. The body portion 77 in the heat dissipation sheet is a portion sandwiched between the electronic circuit board 24 and the backing member 26, and a front surface of the body portion 77 is joined to the peripheral region on the back surface of the electronic circuit board 24. The right wing 50 and the left wing 52 have first portions 50a and 52a connected to the body portions 77 and passing through the slits 16A, and second portions 50b and 52b connected to the first portions 50a and 52a and serving as an extension which extends vertically upward. The second portions 50b and 52b are folded and adhered on the outer surface of the heat discharge shell 16. More specifically, a pair of recesses 16B are formed on the outer wall surface of the heat discharge shell 16, and the pair of the second portions 50b and 52b are housed and fixed inside the recesses 16B. Therefore, the heat generated in the electronic circuit board 24 is conducted directly to the outer surface of the heat discharge shell 16 through the right wing 50 and the left wing 52. A depth of the recess 16B corresponds to a thickness obtained by adding a thickness of each of the wings 50 and 52 and a thickness of the adhesive. In a state where the second portions 50b and 52b are housed in the recesses 16B, a flat-surface state is formed. Alternatively, during the adhesion of the members, in order to achieve a superior thermal conductivity, there may be used an adhesive in which a heat conductive filler is mixed. Alternatively, grease having a heat conductive characteristic may be applied on the joining surface.

A pair of depressions 16C are formed on both sides in the Y direction on the inner surface of the heat discharge shell 16, and the ends of the backing case 33 are inserted into the depressions 16C. In other words, the backing case 33 is held and fixed by the heat discharge shell 16. Because the backing case 33 is fixed by the heat discharge shell 16 and the right wing 50 and the left wing 52 are fixed with respect to the heat discharge shell 16, the inner assembly 14 is reliably fixed to the heat discharge shell 16. As described above, the heat dissipation sheet has the rear wing 30 and the front wing 32, which are joined and fixed to the backing case 33. This structure also contributes to the fixation action of the inner assembly 14.

Figure 3:
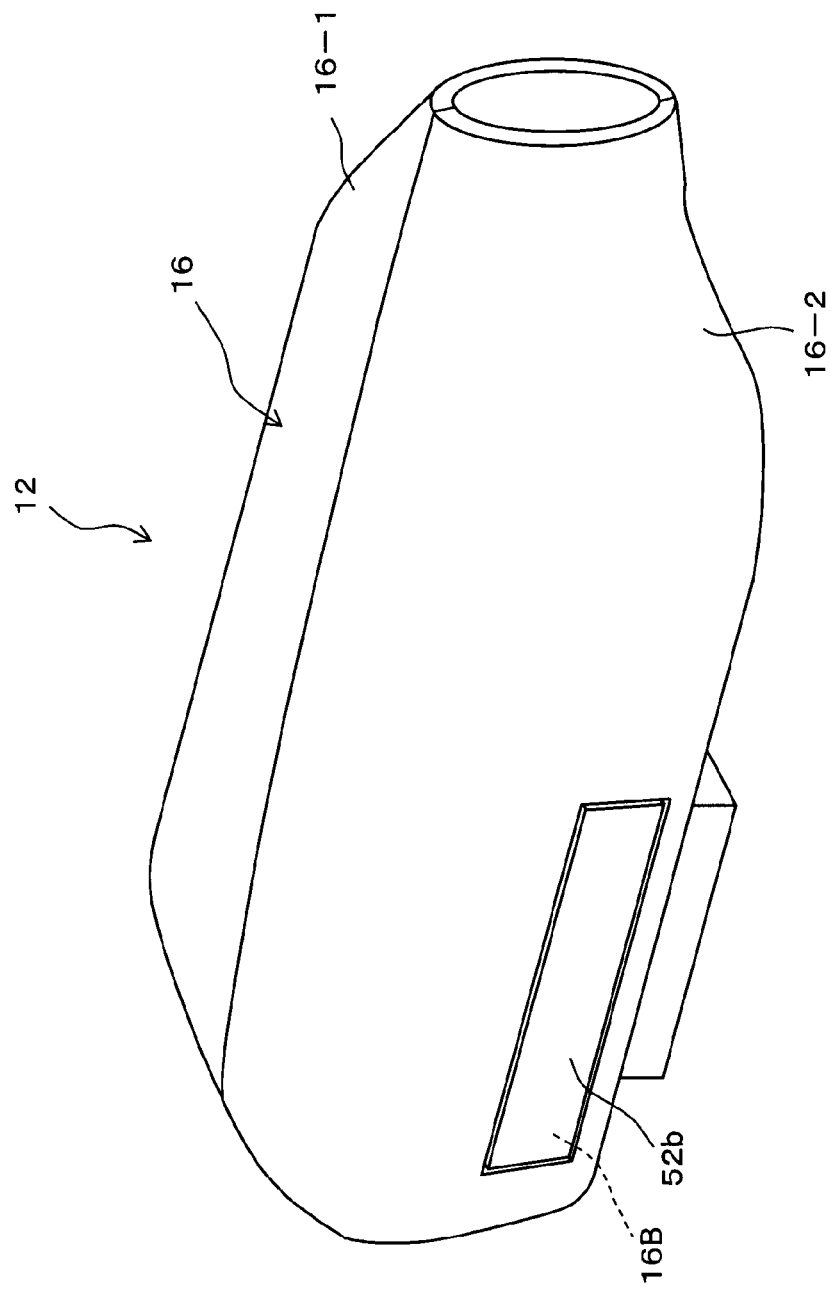
FIG. 3 is a perspective diagram showing a heat discharge shell forming a probe head case.

FIG. 3 is a perspective diagram of the heat discharge shell 16 described above. The heat discharge shell 16 is divided into 2 parts in the left-and-right direction, and is formed from a right side portion 16-1 and a left side portion 16-2 . As described above, the slits 16A are formed on the right side surface and the left side surface of the heat discharge shell 16, the right wing and the left wing are inserted into the respective slits 16A, and the right and left wings are fixed in a folded state. In FIG. 3, the second portion 52b of the left wing is shown. As shown in FIG. 3, the heat discharge shell 16 forms a structure as an outer skeleton, and has a very large surface area. Therefore, when the heat generated in the electronic circuit is conducted to the heat discharge shell 16, the heat discharge shell 16 as a whole can effectively discharge the heat to the outside environment. The outside environment in this case includes the periphery of the probe head through the outer skin, and also the insertion tube and the large number of signal lines or the like passing inside the insertion tube. With such a configuration, the generated heat can be absorbed with the large member while avoiding a local temperature increase, and, by discharging the absorbed heat through the large area, the temperature increase in the electronic circuit board can be effectively inhibited, and, consequently, the temperature increase of the array transducer and the transmission/reception surface can be effectively inhibited. In particular, in the present embodiment, the heat discharge shell 16 functions as a fixing member of the inner assembly 14; that is, the connection structure for fixation can be used as the heat dissipation structure, and, thus, an advantage can be obtained also from the viewpoint of the number of components.

Figure 4:
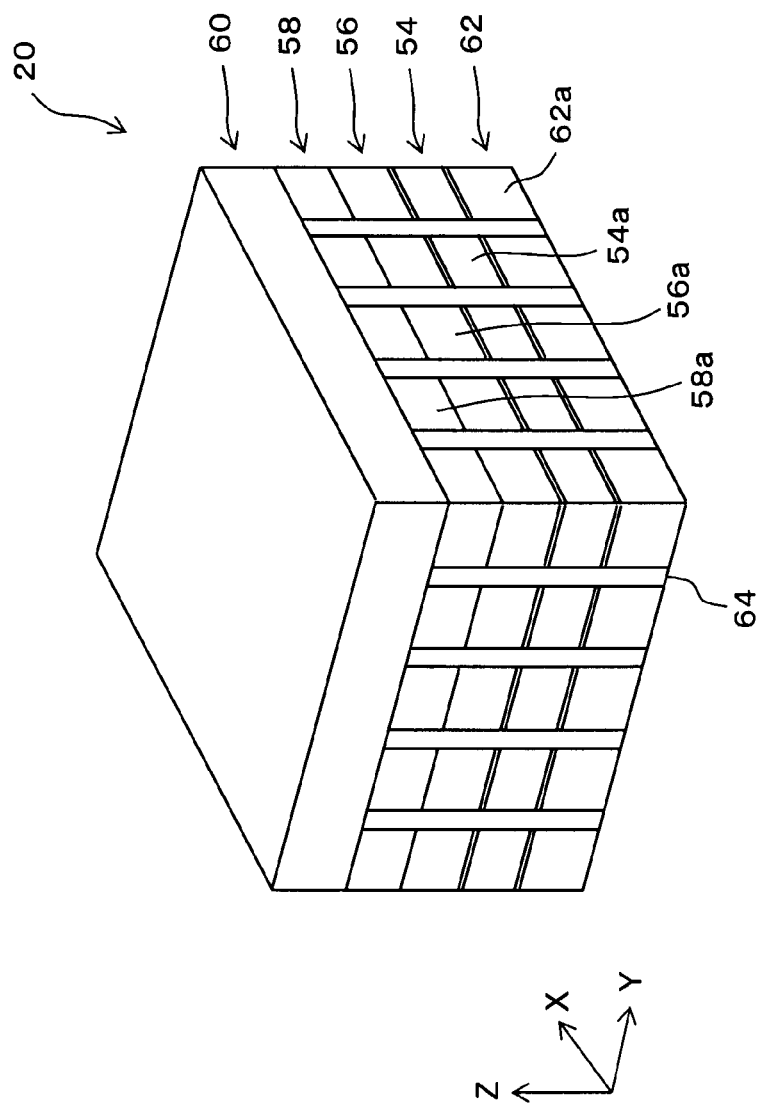
FIG. 4 is a diagram showing an example of a transducer unit.

FIG. 4 shows a specific example of the transducer unit 20 shown in FIG. 1. In FIG. 4, an upper part on the page is the living body side. The array transducer 54 is formed from a plurality of transducer elements 54a arranged along the X direction and the Y direction. The array transducer 54 is formed from a material such as, for example, PZT (piezoelectric zirconate titanate), quartz, zinc oxide, or the like, or is formed from a composite material including such a piezoelectric material. The array transducer may also be formed by MUT. The thickness of the individual transducer element 54a in the Z direction is set to around $\frac{1}{4}\lambda$ with reference to a center frequency of the ultrasound.

A resonance layer 62 having a conductive characteristic is provided on the back surface side of the array transducer 54. The resonance layer 62 is formed by a plurality of resonance elements 62a arranged along the X direction and the Y direction. The resonance layer 62 assists the transmission and reception of the ultrasound at the array transducer 54. The resonance layer 62 is formed from a material having a conductive characteristic, and is formed, for example, as a composite structure including cobalt, zirconia, a tungsten compound, or the like. The materials described in the present specification are merely exemplary. An acoustic impedance in the array transducer 54 is, for example, about 30 MRayls, and the acoustic impedance of the resonance layer 62 is, for example, about 70~100 MRayls. In other words, in the present embodiment, the resonance layer 62 forms a hard backing layer, and the array transducer 54 and the resonance layer 62 together transmit and receive the ultrasound. The resonance layer 62 also has an electrical connection function between the array transducer 54 and the interface board. A thin metal foil forming an electrode is provided on an upper surface and a lower surface of each transducer element 54a, and is formed from, for example, gold, silver, etc.

For reference, the acoustic impedances of the members on the back surface side of the array transducer 54 will be described. The acoustic impedance of the interface board shown in FIG. 1 or the like is, for example, about 19 MRayls, and the acoustic impedance of the electronic circuit board is, for example, about 17 MRayls. In other words, the interface board and the electronic circuit board have approximately the same acoustic impedance, and reflection of the ultrasound at the boundary surface of these boards is prevented as much as possible. The acoustic impedance of the backing member is, for example, about 15~25 MRayls, and, with such a setting, the reflection of the ultrasound at the boundary surface between the electronic circuit board and the backing member is prevented to the extent possible. With such a configuration, the ultrasound exiting from the back surface side of the array transducer and the conductive resonance layer naturally reaches the backing member through the interface board and the electronic circuit board, and unnecessary ultrasound exiting to the back surface side is effectively attenuated and absorbed by the backing member. Even if reflection is generated at the back surface of the backing member 26, the reflected wave is also effectively attenuated and absorbed in the backing member. Therefore, the problem of the multiple reflection caused between the transmission/reception surface and the back surface of the backing member can be effectively prevented in cases, for example, in which the ultrasonic probe is left in the air. During the normal ultrasound diagnosis also, the unnecessary ultrasound exiting to the back surface side can be effectively absorbed, to improve image quality.

Referring again to FIG. 4, a first matching layer 56 and a second matching layer 58 are provided on the living body side of the array transducer 54. The first matching layer 56 is formed from a plurality of matching elements 56a which are two-dimensionally arranged, and the second matching layer 58 is formed from a plurality of matching elements 58a which are two-dimensionally arranged. A protection layer 60 is provided on the living body side of the second matching layer 58. The living body side surface forms the transmission/reception surface. Reference numeral 64 shows a separation channel formed between adjacent elements. The separation channel 64 may be an air layer, but in the present embodiment, silicone rubber or the like having acoustic insulating characteristic is filled in the separation channel 64.

Figure 5:
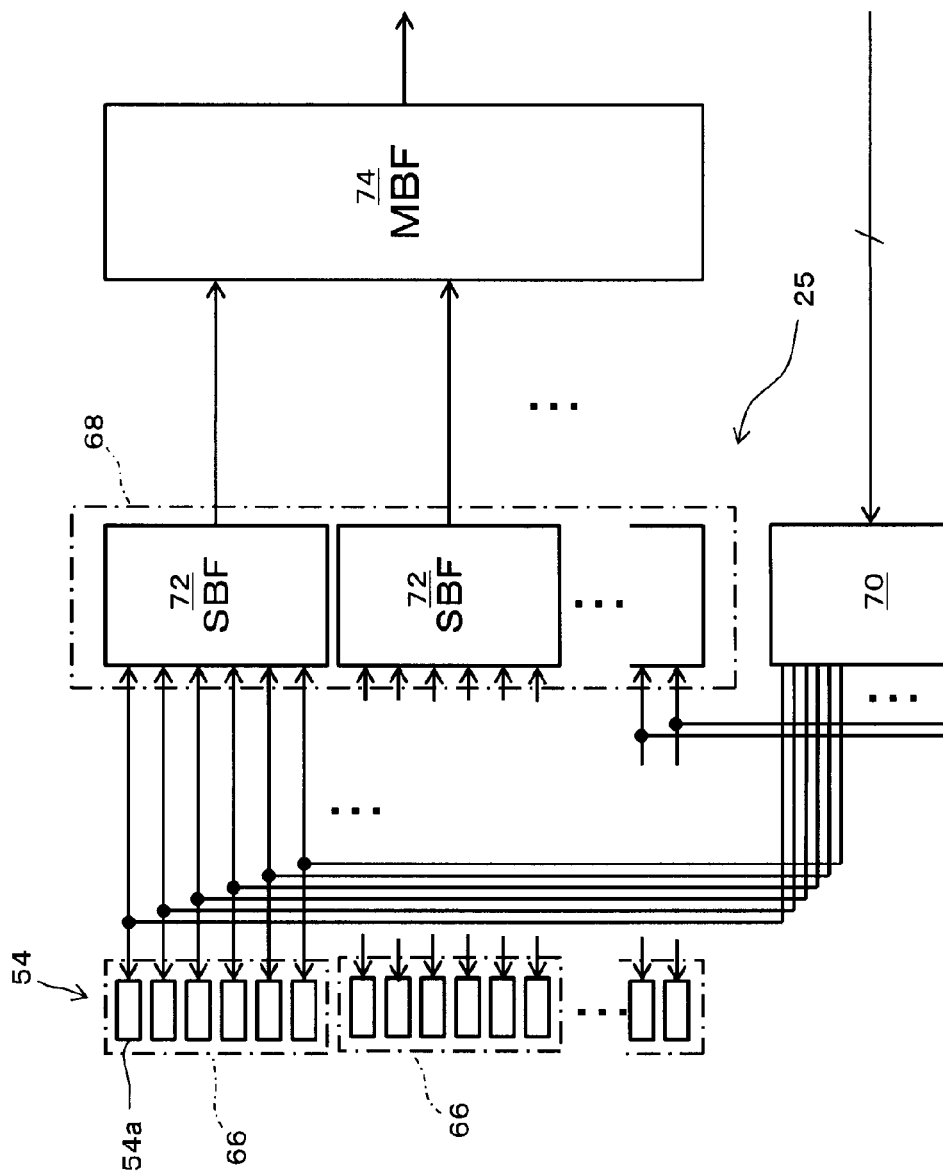
FIG. 5 is a diagram showing an example structure of a transmission and reception circuit.

FIG. 5 shows an example configuration of an electronic circuit 25 of the electronic circuit board. As described above, the array transducer 54 is formed by a plurality of transducer elements 54a which are arranged two-dimensionally. In the present embodiment, a plurality of groups 66 are set for the array transducer 54, and each group 66 is formed from a plurality of transducer elements that are grouped in a predetermined shape. The electronic circuit 25 is formed by a transmission signal processing circuit 70 and a reception signal processing circuit 68. The transmission signal processing circuit 70 generates a plurality of transmission drive signals to be supplied to the plurality of transducer elements based on a transmission control signal (including a transmission trigger signal) from the device body side. One transmission signal processing circuit 70 may be provided for the entirety of the array transducer 54 or the transmission signal processing circuit 70 may be provided for each group 66. In either case, the transmission signal processing circuit 70 generates a plurality of transmission drive signals from one transmission control signal, and realizes a process corresponding to the channel reduction during transmission.

The reception signal processing circuit 68 is formed from a plurality of sub beam formers (SBF) 72 corresponding to the plurality of groups 66 in the present embodiment. Each SBF 72 executes a phased summing process (sub phased summing process) for the plurality of reception signals output from the corresponding group 66, to generate a group reception signal after phased summing. With such a process, a plurality of group reception signals are generated, a main phased summing process is executed at a main beam former (MBF) 74 on the group reception signals, and phase-alignment beam data corresponding to the reception beam are generated. Here, the MBF 74 is provided in the device body. Each SBF 72 executes the channel reduction during reception. In the present embodiment, for example, phased summing process is executed for 16 reception signals, to generate one group reception signal.

As heat is generated in the process of executing the transmission/reception signal processes, unless the heat dissipation process is effectively executed, the temperature of the electronic circuit board would be increased and the temperatures of the array transducer and the transmission/reception surface would also be consequently increased. On the other hand, in the present embodiment, with the above-described heat dissipation process; that is, with a process to conduct heat from the electronic circuit board to the heat discharge shell through the heat dissipation sheet (and the backing case), and with a process to discharge heat over the entirety of the heat discharge shell, it is possible to effectively discharge the heat generated in the electronic circuit board to the outside.

Next, an example operation of the probe shown in FIG. 1 or the like will be described. The probe head 12 shown in FIG. 1 is inserted from a mouth to the esophagus of a subject, and the probe head 12 is positioned at a predetermined position in the esophagus. With this process, the transmission/reception surface of the probe head 12 is set to be in close contact with the inner wall surface of the esophagus. By transmitting and receiving the ultrasound in this state; more specifically, by executing a two-dimensional scan of the ultrasound beam, a three-dimensional region including a measurement site in the heart is formed, and volume data corresponding to the three-dimensional region can be acquired. Based on such volume data, an ultrasound three-dimensional image representing the three-dimensional space is formed, or there is formed an arbitrary tomographic image representing an arbitrary cross section in the three-dimensional space or a tri-plane image representing a plurality of predetermined cross sections.

More specifically, during transmission, a transmission signal is supplied from the device body side through the cable to the probe head 12. The transmission signal is sent through the flexible board 36 or the flexible board 38, and the interface board 22, to the electronic circuit. The transmission signal processing circuit in the electronic circuit generates a plurality of transmission drive signals based on the single transmission signal, and supplies the plurality of signals to the plurality of corresponding transducer elements. In this case, the plurality of transmission drive signals are sent to the array transducer through the lead array formed on the interface board as described above. With the supply of the plurality of the transmission drive signals, a transmission beam is formed in the array transducer. In this process, if unnecessary ultrasound is emitted to the back surface side of the array transducer, the unnecessary ultrasound is effectively absorbed and reduced by the backing member 26.

On the other hand, during the reception, when a reflected wave from the inside of the living body is received by the array transducer, a plurality of reception signals are sent from the array transducer to the electronic circuit through the lead array 40 on the interface board 22. In the reception signal processing unit of the electronic circuit, a sub phased-summing process is executed for the plurality of reception signals in units of each group, to generate group reception signals. A plurality of group reception signals generated in this manner are transmitted to the plurality of signal lines through the flexible board 36 and the flexible board 38, and further to the device body. In the device body, the main phased-summing process is executed based on the plurality of group reception signals, to generate beam data corresponding to the reception beam. During the reception, even if the reflected wave appears on the back surface side of the array transducer, such unnecessary ultrasound is effectively reduced by the backing member 26.

Next, thermal action will be described. The heat generated at the electronic circuit by the transmission/reception signal processes or the like is conducted to the heat discharge shell 16 through the heat dissipation sheet joined on the back surface side of the electronic circuit board 24. Specifically, the heat conducted to the rear wing 30 and the front wing 32 of the heat dissipation sheet is conducted through the backing case 33 to the heat discharge shell 16. On the other hand, the heat conducted to the right wing and the left wing of the heat dissipation sheet is directly conducted to the outer surface of the heat discharge shell 16. In this manner, the heat can be effectively conducted to the heat discharge shell 16 through 4 wings. Because the heat discharge shell 16 is formed as a member having a very large thermal capacity and having a very large surface area, the conducted heat can be effectively discharged to the outside, and local heat generation can be prevented.

In the present embodiment, the thermal conductivity of the electronic circuit board 24 and the heat dissipation sheet is set higher than the thermal conductivity of the interface board 22, and thus, a large part of the heat generated in the electronic circuit board is conducted to the heat dissipation sheet. In other words, the interface board has a certain heat separation function, and even if there is heat conduction by the lead array 40, heat conduction to the array transducer through the interface board 22 is inhibited.

In the present embodiment, as described above, the backing member 26 is joined on the center part on the back surface of the electronic circuit board 24, and the heat dissipation sheet is joined at the peripheral region on the back surface. With such a configuration, the backing function provided by the backing member can be applied to a part where the propagation of the ultrasound tends to occur more easily, to effectively absorb the unnecessary ultrasound. On the other hand, in the peripheral region, heat conduction similar to that in the center region occurs, and heat can be effectively taken away from the peripheral region through the heat dissipation sheet. In other words, on the back surface side of the electronic circuit board, both absorption of the unnecessary ultrasound and heat dissipation for inhibiting heat generation can be realized. In particular, in the above-described embodiment, the backing member 26 is housed in the backing case 33, and the backing case 33 is surrounded by the rear wing 30 and the front wing 32. Thus, an outer skeleton can be constructed around the backing member 26 which is in general soft, and the entirety of the inner assembly 14 can be fixed by holding the backing member 26. As a result, firm holding of the inner assembly 14 on the living body side becomes not necessary. Alternatively, other fixation methods may be used for holding the inner assembly 14 as necessary.

Next, a manufacturing method of the probe shown in FIG. 1 will be described with reference to FIGS. 6~11.

Figure 6:
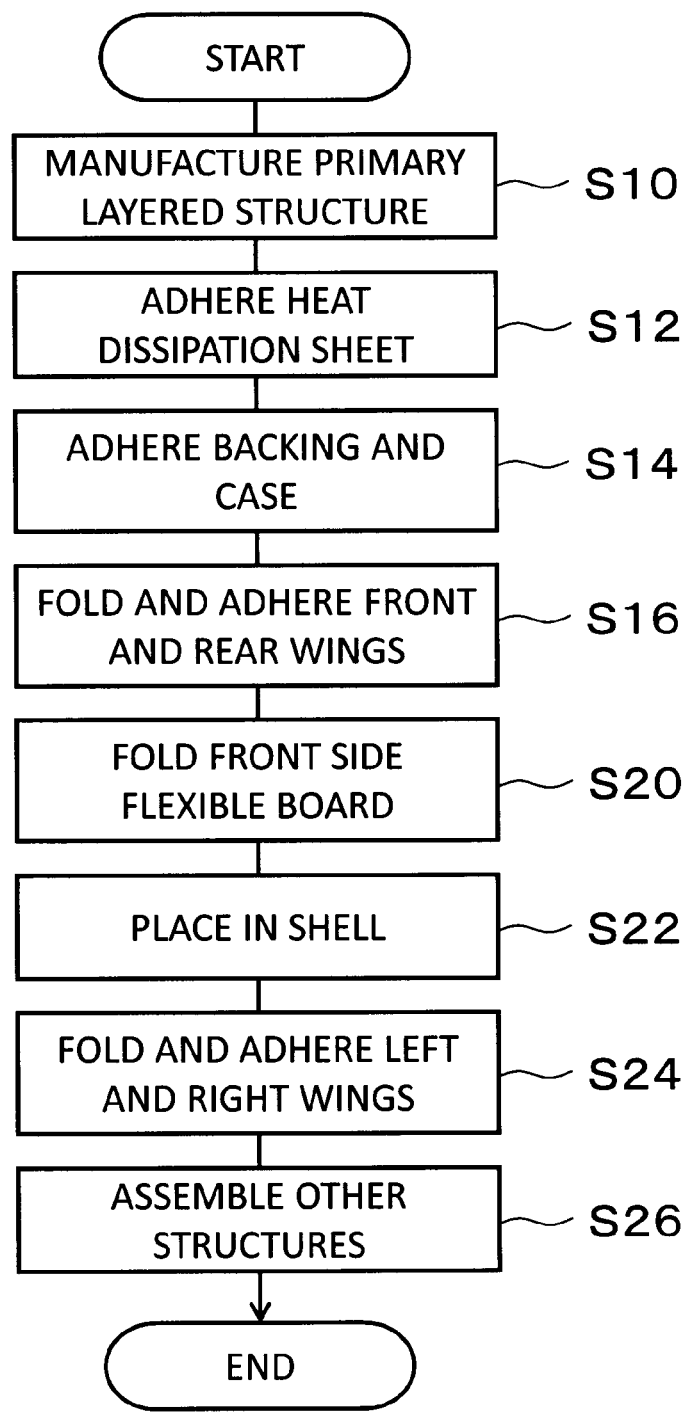
FIG. 6 is a flowchart showing an example method of manufacturing a probe according to a preferred embodiment of the present invention.
Figure 7:
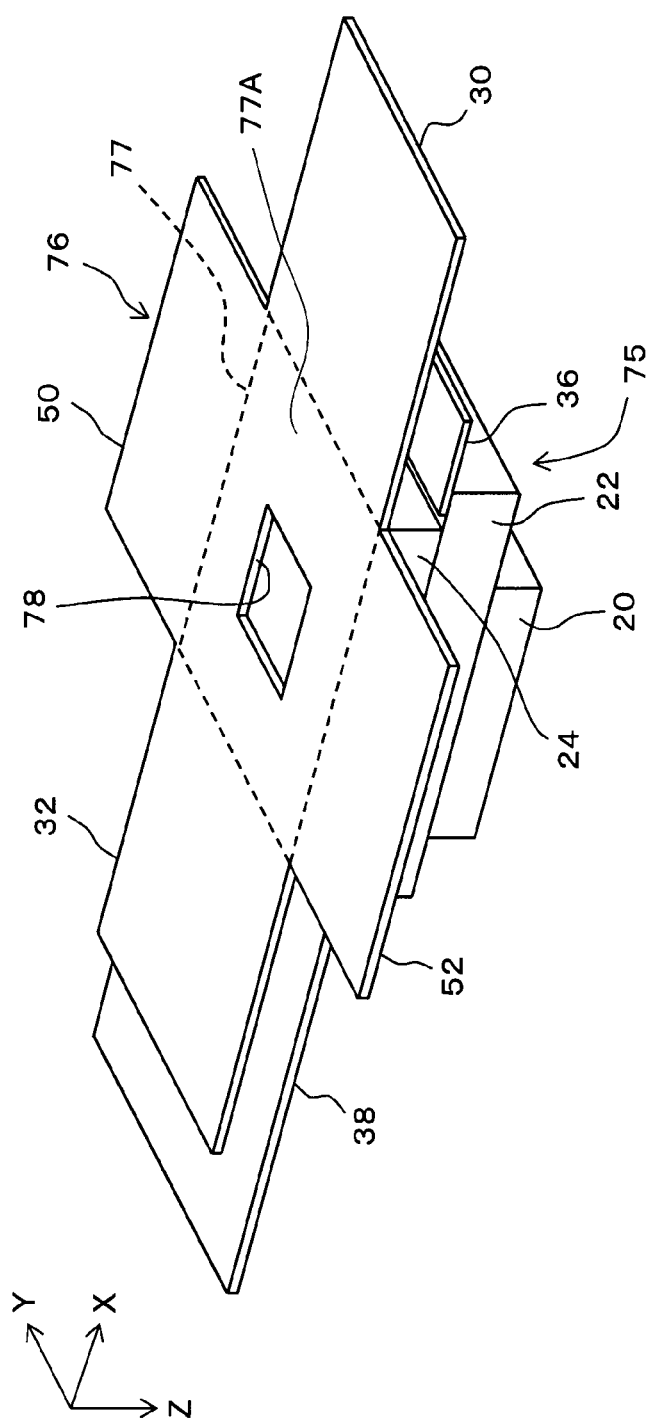
FIG. 7 is a diagram for explaining adhesion of a heat dissipation sheet to a primary layered structure.

In S10 in FIG. 6, a primary layered structure 75 shown in FIG. 7 is manufactured. That is, the primary layered structure 75 including the transducer unit 20, the interface board 22, and the electronic circuit board 24 is formed. The flexible boards 36 and 38 are attached to the interface board 22.

In S12 of FIG. 6, as shown in FIG. 7, a heat dissipation sheet 76 is adhered onto the primary layered structure 75. The heat dissipation sheet 76 includes the body portion 77 having an opening 78, and a plurality of wings connected thereto. The plurality of wings include the rear wing 30 and the front wing 32 arranged along the X direction, and the right wing 50 and the left wing 52 arranged along the Y direction. Reference numeral 77A shows an area corresponding to the peripheral region on the back surface of the electronic circuit board 24. The form of the heat dissipation sheet 76 is not limited to that shown in FIG. 7.

Figure 8:
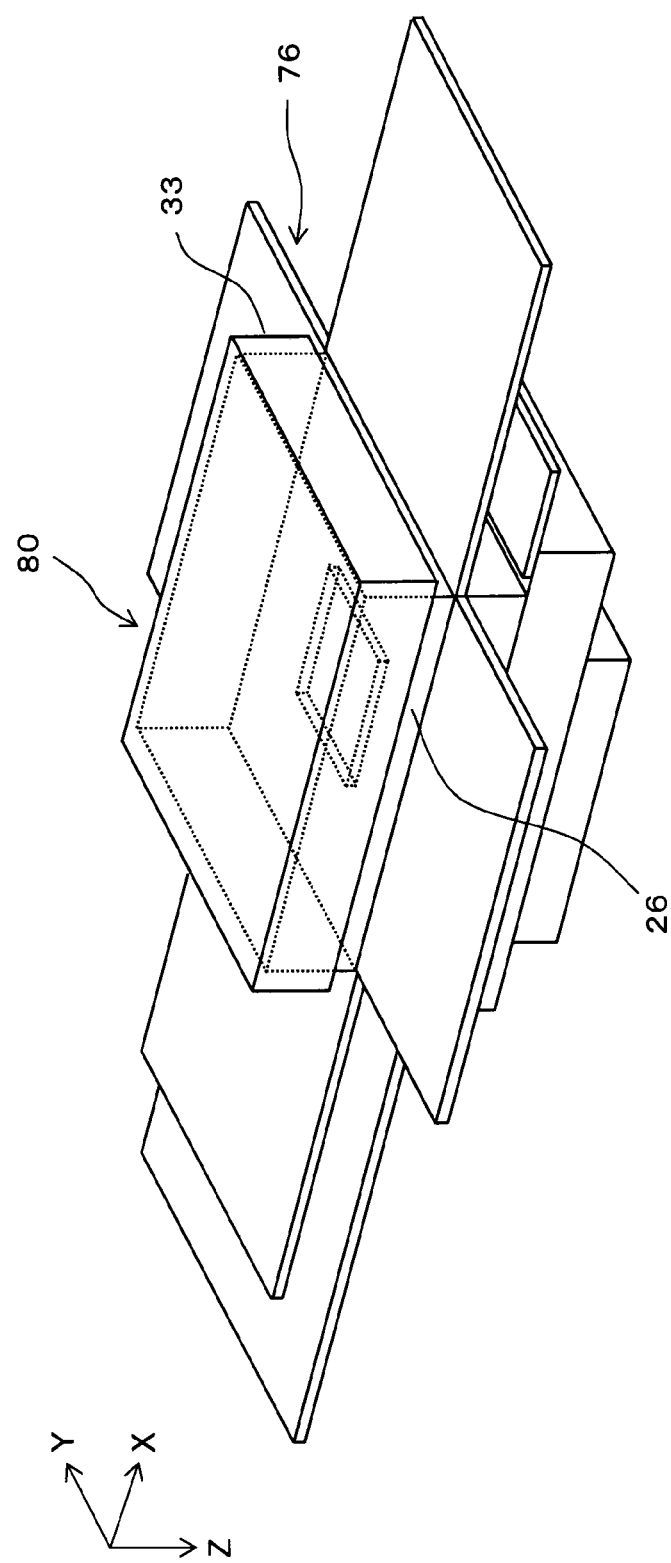
FIG. 8 is a diagram for explaining adhesion of a backing and a case.
Figure 9:
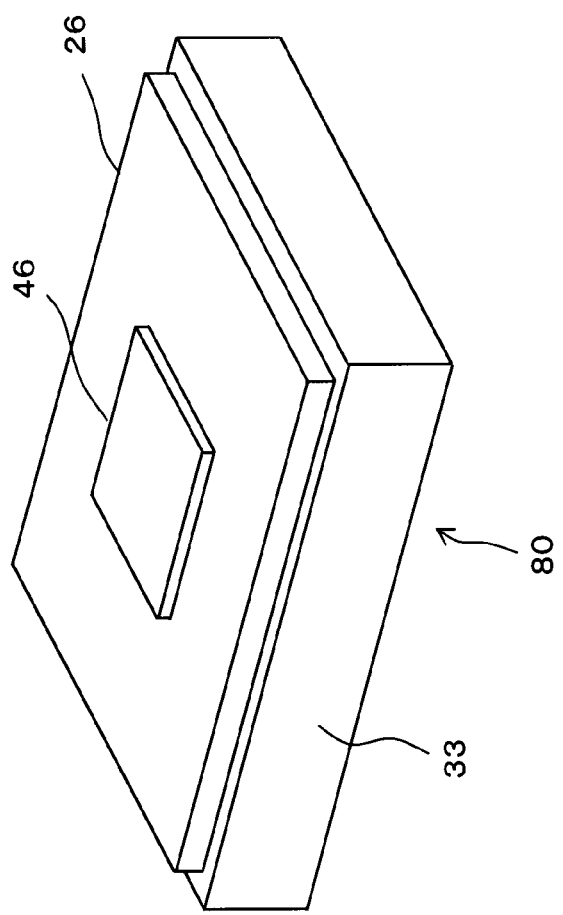
FIG. 9 is a diagram showing a protrusion provided on the backing.

In S14 of FIG. 6, the backing member and the backing case are adhered to the primary layered structure to which the heat dissipation sheet is adhered. Specifically, as shown in FIG. 8, a combined structure 80 is joined on the heat dissipation sheet 76. The combined structure 80 is formed from the backing member 26 and the backing case 33 housing the backing member 26. FIG. 9 shows a state where the combined structure 80 is placed upside down, and a projection 46 is formed on the center part on the living body side of the backing member 26. The combined structure is adhered on the heat dissipation sheet in such a manner that the projection 46 is fitted to the opening 78 shown in FIG. 7.

Figure 10:
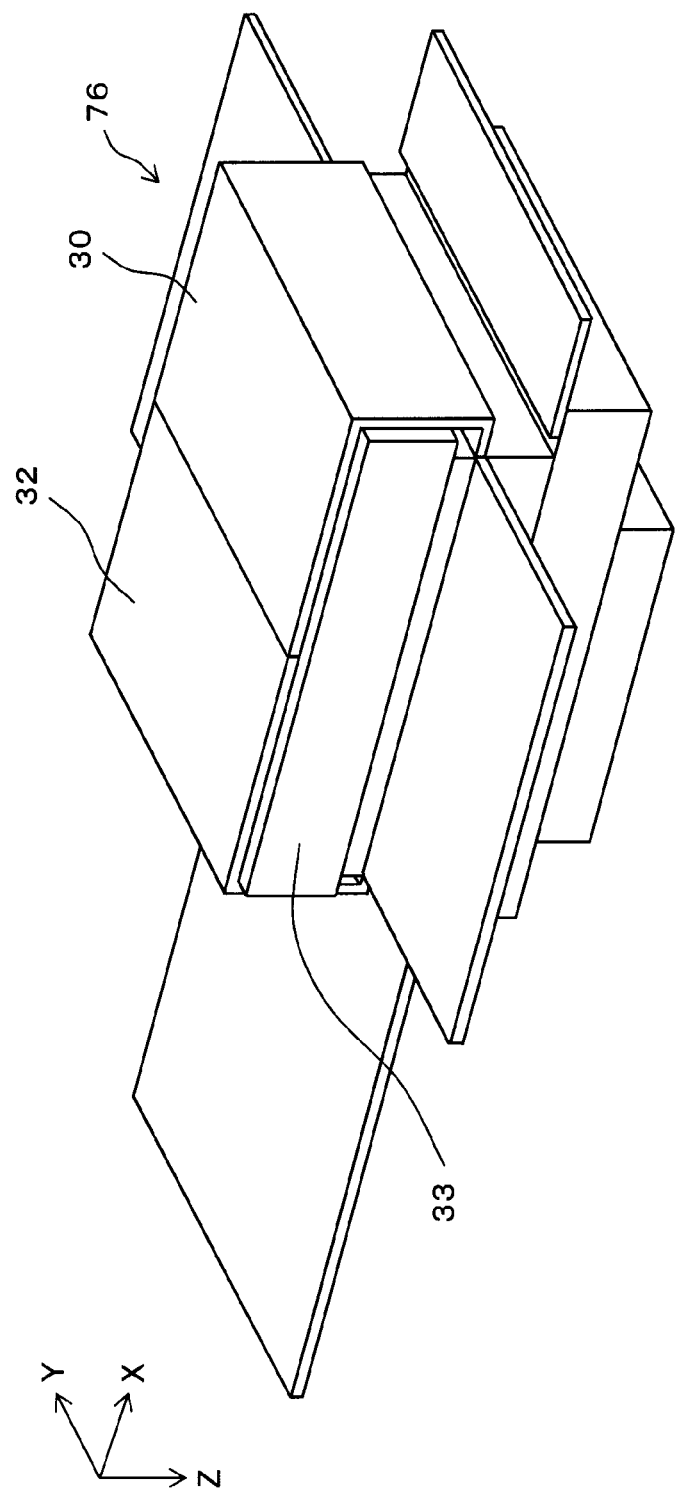
FIG. 10 is a diagram for explaining folding and adhesion of front and rear wings.

In S16 of FIG. 6, as shown in FIG. 10, the rear wing 30 and the front wing 32 are folded in the back surface side of the backing case 33; that is, the upper side in FIG. 10, and adhered and fixed. With this process, the backing case 33 and the heat discharge sheet 76 are integrated.

Figure 11:
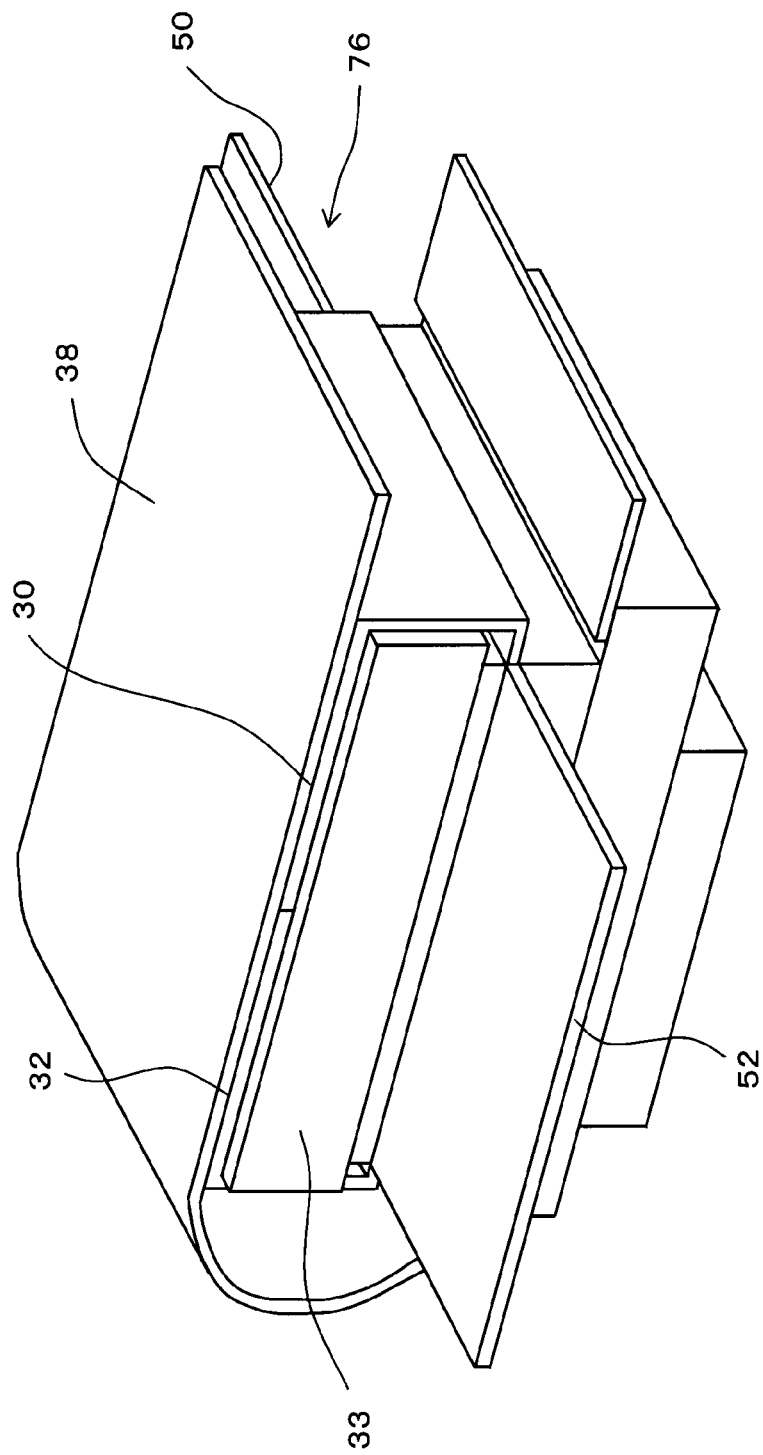
FIG. 11 is a diagram for explaining folding of a front side flexible board.

In S20 of FIG. 6, as shown in FIG. 11, the front side flexible board 38 is folded. Specifically, the front side flexible board 38 is folded to pass through the non-living body side of the backing case 33.

In S22 of FIG. 6, the assembly shown in FIG. 11 is placed in the heat discharge shell. Specifically, the heat discharge shell is assembled such that the backing case is sandwiched between two divided components, and, at the same time, the right wing and the left wing extend to the outside from the pair of the slits, and the inner assembly is placed within the heat discharge shell. In S24 of FIG. 6, the portions of the right wing and the left wing protruding from the slits are folded, and are adhered and fixed on the heat discharge shell. In S26 of FIG. 6, a wiring process, formation of the outer skin on the outer side of the heat discharge shell, and the like are executed, to form the probe as shown in FIG. 1.

As is clear from the above description, the rear wing and the front wing at the heat dissipation sheet achieve the fixation function of the backing case; that is, the backing member, and the right wing and the left wing at the heat dissipation sheet achieve a function to surround further from the outside the heat discharge shell which sandwiches the backing case. As a result of such multiple surrounding, the inner assembly is firmly fixed on the heat dissipation shell, and, at the same time, a reliable heat conduction route from the inner assembly to the heat discharge shell is constructed.

Figure 12:
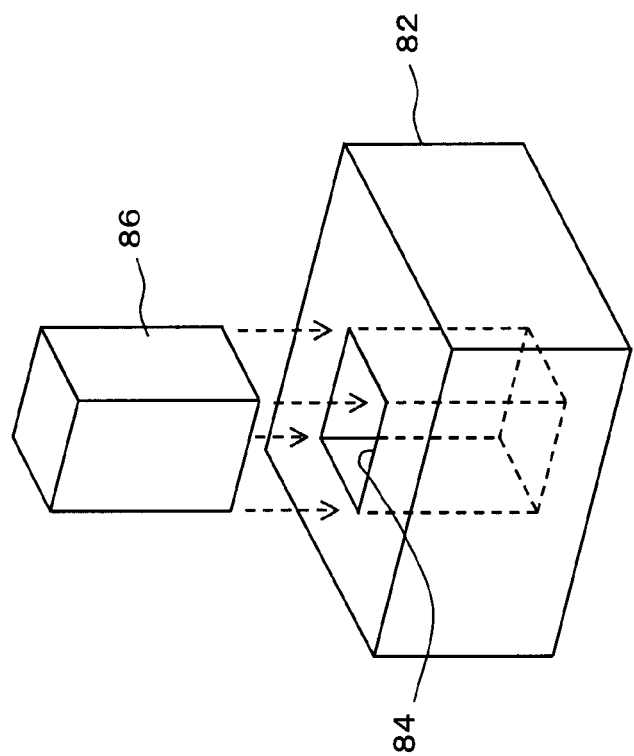
FIG. 12 is a diagram showing a backing and a heat dissipation member according to another preferred embodiment of the present invention.

FIG. 12 shows another preferred embodiment of the present invention. In the example configuration of FIG. 12, a heat dissipation member 82 is formed as a block-shaped member, and an opening 84 is formed at a center part thereof. A backing member 86 is inserted and fixed in the opening 84. This composite structure is joined to the back surface side of the electronic circuit board.

In such an embodiment also, the backing member 86 can be joined to the center part on the back surface side of the electronic circuit board; that is, a part where the ultrasound propagation most easily occurs, and, because the heat dissipation member 82 is joined at the periphery, sufficient heat absorption can be realized by the heat dissipation member 82. In other words, with such a configuration, both the absorption function of the ultrasound and the heat dissipation function can be achieved.

Figure 13:
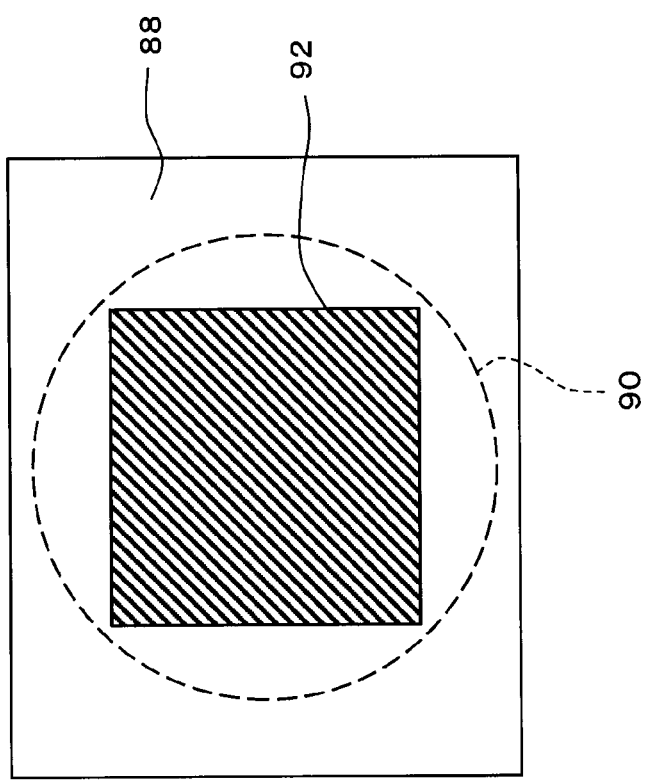
FIG. 13 is a diagram showing a relationship between a transmission/reception region and the backing member joining region.

FIG. 13 shows a two-dimensional region 88 corresponding to the array transducer. Reference numeral 90 shows an effective region actually used for transmission and reception, and is a circular region. In the setting of the region for joining the backing member, preferably, there is set a region having an area greater than or equal to 50 percent that of the entire region of the array transducer; specifically, the region at the center. In particular, as shown in FIG. 13, the backing region is preferably set as a region 92 which inscribes the effective region 90 actually used for transmission or reception or an equivalent region. According to such a configuration, the backing function may be achieved approximately uniformly over the entire array transducer.

The probe in the above-described embodiment is an esophagus probe, but the above-described structure may be applied to other body cavity insertion type probes, and also to probes other than the body cavity insertion type probe.

Figure 14:
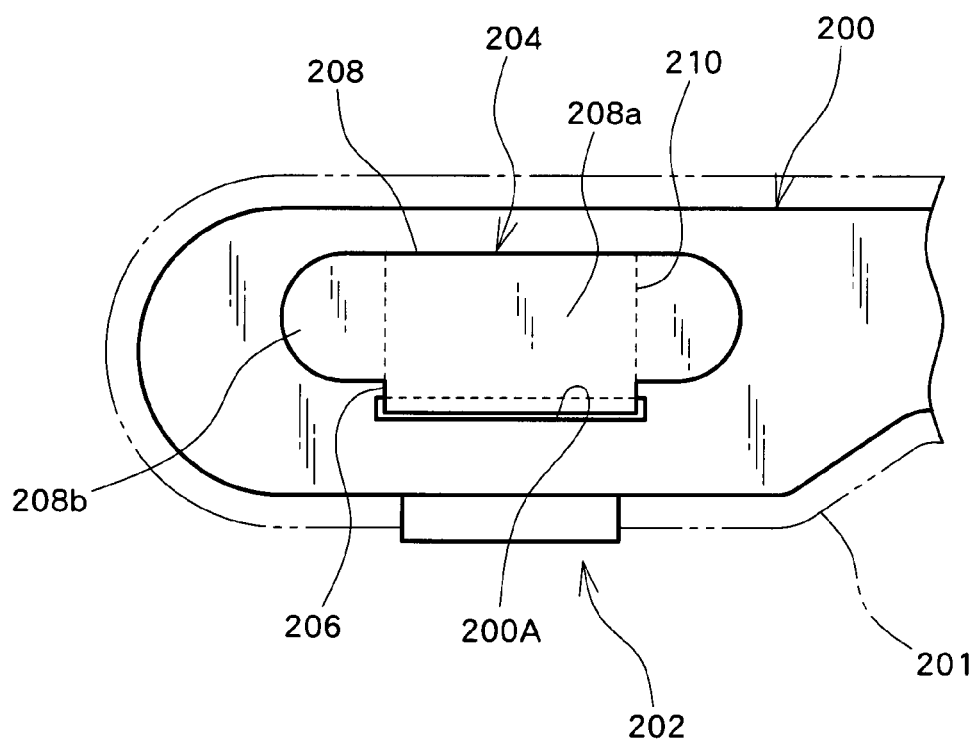
FIG. 14 is a diagram showing a second example fixation method of the wing.
Figure 15:
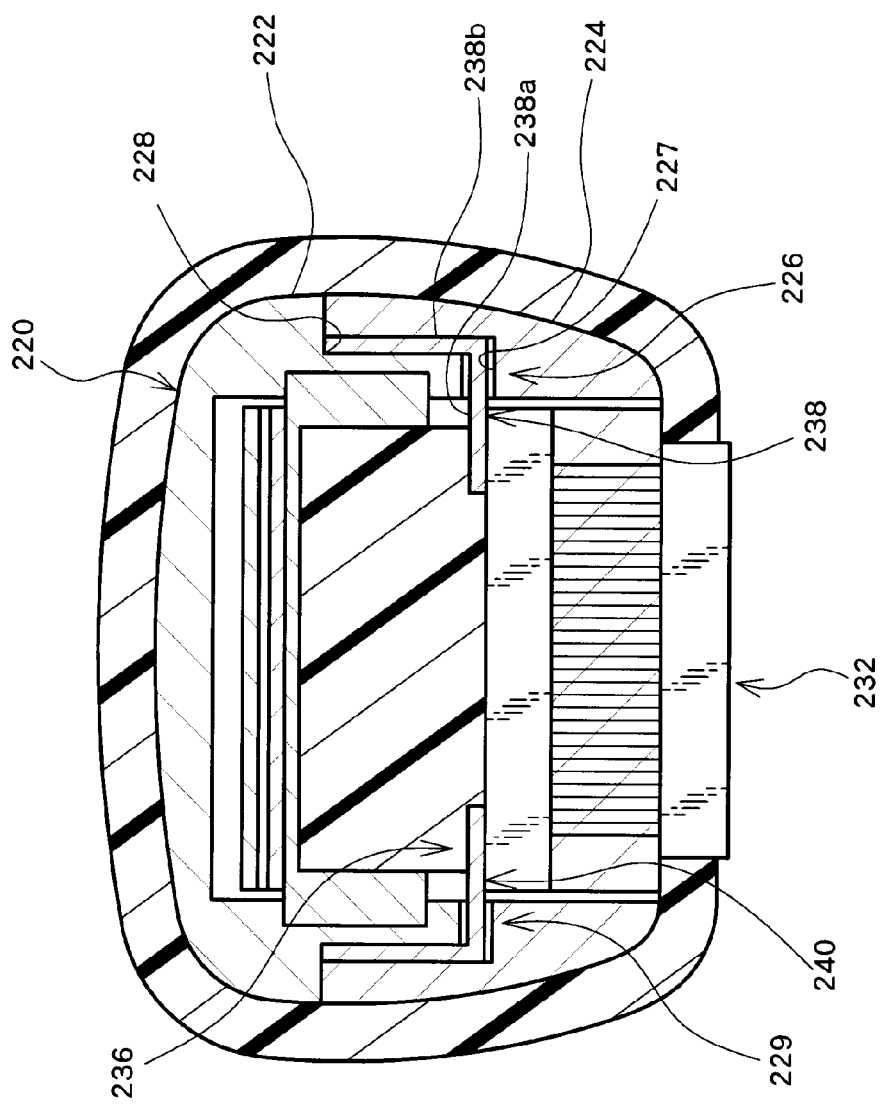
FIG. 15 is a diagram showing a third example fixation method of the wing.

FIGS. 14 and 15 are diagrams showing second and third examples of a method of fixing the wings. Similar to the first example shown in FIG. 2, the second and third examples also allow heat generated in the electronic circuit board to be discharged to the probe head case serving as the heat discharge shell, using the heat dissipation sheet.

FIG. 14 shows the second example of the wing fixation method. In the second example method, an inner unit 202 serving as the inner assembly is housed in a hollow probe head case 200. The inner unit 202 is a layered structure including the array transducer, the electronic circuit board, the heat dissipation sheet, and the like. The heat dissipation sheet comprises a body portion joined to a back surface of the electronic circuit board, and a plurality of wings extending from the body portion. The plurality of wings include a left wing 204 and a right wing (not shown). The right wing has the same shape as the left wing 204, and is fixed by the same method as that for the left wing 204. Thus, in the following description, the left wing 204 is described as a representative wing, for describing the structure and the fixation method thereof.

FIG. 14 shows a fixed state of the left wing 204. The left wing 204 has a first portion 206 which passes through a slit 200A, and a second portion 208 which is an extension portion (or an end) connected to the first portion 206. A lateral width of the first portion 206 is smaller than a lateral width of the slit 200A. The second portion 208 can be deformed from a folded state to an open state. The second portion 208 includes a rectangular portion 208a and both end portions 208b provided on both ends of the rectangular portion 208a. The end portions 208b are the portions that can be folded. The lateral width of the rectangular portion 208a is the same as the lateral width of the first portion 206. When the second portion 208 passes through the slit 200A, the second portion 208 is set in the folded state. With such a configuration, the second portion 208 can easily pass through the slit 200A. After the second portion 208 passes through the slit 200A, the second portion 208 is set in the open state. In the open state, the lateral width of the second portion 208 is greater than the lateral width of the slit 200A. The second portion 208 in the open state is adhered and fixed on the outer surface of the probe head case. Alternatively, a recess may be formed on the outer surface of the probe head case corresponding to the shape of the second portion 208. The second portion in the right wing can also be deformed from the folded state to the open state, and the second portion is joined and fixed on the outer surface of the probe head case in the open state. Reference numeral 210 represents a folding line, and reference numeral 201 represents an outer skin.

According to the second example method shown in FIG. 14, the joining portion in the wing with the probe head case can be enlarged, and thus, the heat conduction efficiency can be improved. In particular, there is an advantage that the lateral width of the slit does not need to be set unnecessarily large. As the shape of the second portion 208, various shapes may be employed. For example, the second portion may be configured to open in both the upper and lower directions on the outer surface of the probe head case.

FIG. 15 shows a third example of the wing fixation method. A probe head case 220 is formed by an upper case 222 and a lower case 224, which are combined in the up-and-down direction (Z direction). Opening structures 226 and 229 are formed on a right side and a left side over the upper case 222 and the lower case 224. These opening structures 226 and 229 have structures symmetric from each other, and therefore, the opening structure 226 will be described below as a representative structure.

The opening structure 226 is formed by a horizontal groove 227 which is in communication with the inside of the probe head case 220, and a vertical groove 228 in communication with the horizontal groove. The horizontal groove 227 has an inlet opening, and a side deeper from the inlet opening forms a gap. An inner unit 232 placed in the probe head case 220 comprises the array transducer, the electronic circuit board, a heat dissipation sheet 236, and the like. The heat dissipation sheet 236 includes a body portion and a plurality of wings extending from the body portion, and the plurality of wings include a right wing 238 and a left wing 240. The wings are flexible. In FIG. 15, the right wing 238 is inserted into the opening structure 226. The right wing 238 has a first portion (horizontal portion) 238a connected to the body portion, and a second portion (vertical portion) 238b connected to the first portion 238a. The first portion 238a is inserted into the horizontal groove 227 and the second portion is inserted into the vertical groove 228. In such an inserted state, the right wing 238 is sandwiched and fixed by the upper case 222 and the lower case 224. Similarly, the left wing 240 is inserted into the opening structure 229 and is sandwiched and fixed by the upper case 222 and the lower case 224.

According to the structure shown in FIG. 15, the heat generated in the electronic circuit board can be conducted to the inside of the probe head case 220 through two wings inserted in the wall thickness of the probe head case 220. In the probe head case 220, in general, more temperature reduction can be expected from the inner surface toward the outer surface, and, thus, it is more preferable to conduct the heat to a part other than the inner surface rather than to the inner surface. According to the structure shown in FIG. 15, the heat can be conducted to the inside in which a higher temperature reduction advantage can be expected than in the case of the inner surface. In addition, both surfaces in the wing can be contacted with the probe head case 220, resulting in effective heat dissipation. Moreover, the two wings can be sandwiched when the upper case 222 and the lower case 224 are combined, and thus, the two wings can be fixed in a simple manner. Alternatively, the wings may be fixed using an adhesive or the like. In FIG. 15, the wings are folded in the upper direction (non-living body side), but alternatively, the wings may be folded in the lower direction (living body side). By dissipating the heat on the right side and the left side of the inner unit, the distance from the heat generating structure to the heat discharge structure can be shortened, and an advantage can be obtained that the heat dissipation efficiency can be improved.

The invention claimed is:

1. An ultrasonic probe, comprising:
an inner unit including an array transducer having a plurality of transducer elements, an electronic circuit board provided on a side of a back surface of the array transducer and having an electronic circuit which is electrically connected to the plurality of transducer elements, and a heat dissipation sheet that conducts heat from the electronic circuit board; and
a probe head case that houses the inner unit, wherein the heat dissipation sheet comprises:
a body portion that receives the heat from the electronic circuit board; and
a wing which is a portion to which heat from the body portion is conducted and which extends from the body portion toward an outer side,
the probe head case has an opening structure, and
the wing is inserted into the opening structure and is joined to the probe head case.

2. The ultrasonic probe according to claim 1, wherein at least the wing in the heat dissipation sheet is flexible.

3. The ultrasonic probe according to claim 1, wherein
the heat dissipation sheet has a right side wing and a left side wing that extend from the body portion toward a right side and a left side, respectively,
the probe head case has a right side opening structure and a left side opening structure,
the right side wing is inserted into and fixed on the right side opening structure, and
the left side wing is inserted into and fixed on the left side opening structure.

4. The ultrasonic probe according to claim 3, wherein
the right side opening structure and the left side opening structure are a right side slit and a left side slit in communication with an inside and an outside of the probe head case,
the right side wing is inserted into the right side slit and is fixed on an outer surface of the probe head case, and
the left side wing is inserted into the left side slit and is fixed on the outer surface of the probe head case.

5. The ultrasonic probe according to claim 4, wherein
a right side recess in communication with the right side slit is formed on the outer surface of the probe head case, and an end of the right side wing is housed in the right side recess, and
a left side recess in communication with the left side slit is formed on the outer surface of the probe head case, and an end of the left side wing is housed in the left side recess.

6. The ultrasonic probe according to claim 1, wherein
the wing comprises:
a first portion having a lateral width which allows the wing to pass through the opening structure; and
a second portion which is a portion connected to the first portion, which can be opened, which has a greater lateral width than that of the first portion in an open state, and which is fixed on the outer surface of the probe head case in the open state.

7. The ultrasonic probe according to claim 1, wherein
the probe head case is formed from a first case portion and a second case portion,
a gap is formed in the opening structure between the first case portion and the second case portion, and
the wing is inserted into the gap.

* * * * *